United States Patent [19]

Wiest

[11] 4,156,652
[45] May 29, 1979

[54] APPARATUS FOR STERILIZING FLUIDS WITH UV RADIATION AND OZONE

[76] Inventor: Reiner Wiest, Gartenstrasse 52, 7312 Kirchheim-Teck, Fed. Rep. of Germany

[21] Appl. No.: 819,890

[22] Filed: Jul. 28, 1977

[51] Int. Cl.$^2$ .......................... C02B 1/38; C02B 3/02; C02B 3/08
[52] U.S. Cl. ................................. 250/527; 210/63 Z; 210/205; 210/256; 250/430; 250/436; 250/438; 422/199; 422/305
[58] Field of Search ............ 21/54 R, 102 R, DIG. 2, 21/74 A, 104; 62/3; 210/63 Z, 205, 256; 250/430, 436, 438, 527

[56] References Cited

U.S. PATENT DOCUMENTS

| | | | |
|---|---|---|---|
| 1,312,484 | 8/1919 | Knox et al. | 21/74 A |
| 3,481,692 | 12/1969 | Linder | 21/104 |
| 3,750,556 | 8/1923 | Duke et al. | 21/74 A |
| 3,970,426 | 7/1976 | Stark et al. | 21/DIG. 2 |
| 4,049,552 | 9/1977 | Arf | 21/74 A |
| 4,065,936 | 1/1978 | Fenton et al. | 62/3 |

FOREIGN PATENT DOCUMENTS

| | | | |
|---|---|---|---|
| 2205598 | 8/1973 | Fed. Rep. of Germany | 21/DIG. 2 |
| 2225984 | 12/1973 | Fed. Rep. of Germany | 21/DIG. 2 |
| 2307877 | 9/1974 | Fed. Rep. of Germany | 21/DIG. 2 |

Primary Examiner—Sidney Marantz
Assistant Examiner—Bradley Garris
Attorney, Agent, or Firm—Michael J. Striker

[57] ABSTRACT

An apparatus for sterilizing fluids comprises a radiation chamber which comprises a source of ultraviolet radiation; a housing surrounding said source and including an inner casing permeable to ultraviolet radiation and bounding a channel with said source, and an outer casing surrounding said inner casing and forming a treating space therewith; a conduit for conducting a stream of gas containing molecular oxygen through said channel for exposure to said ultraviolet radiation to produce an ozone-enriched gas; a conduit for conducting a fluid through said treating space so as to become sterilized by the ultraviolet radiation; and a conduit for introducing at least a portion of said ozone-enriched gas from said channel into said treating space to become united with said fluid, whereby said introduced portion of ozone-enriched gas is again exposed to ultraviolet radiation in order to produce an increased content of ozone in said ozone-enriched gas and an additional sterilizing effect is produced in said fluid. A process for sterilizing fluid is also provided. According to this process, a fluid and a gas which contains molecular oxygen are irradiated with ultraviolet radiation and are then mixed together in order to produce an additional sterilizing effect.

9 Claims, 1 Drawing Figure

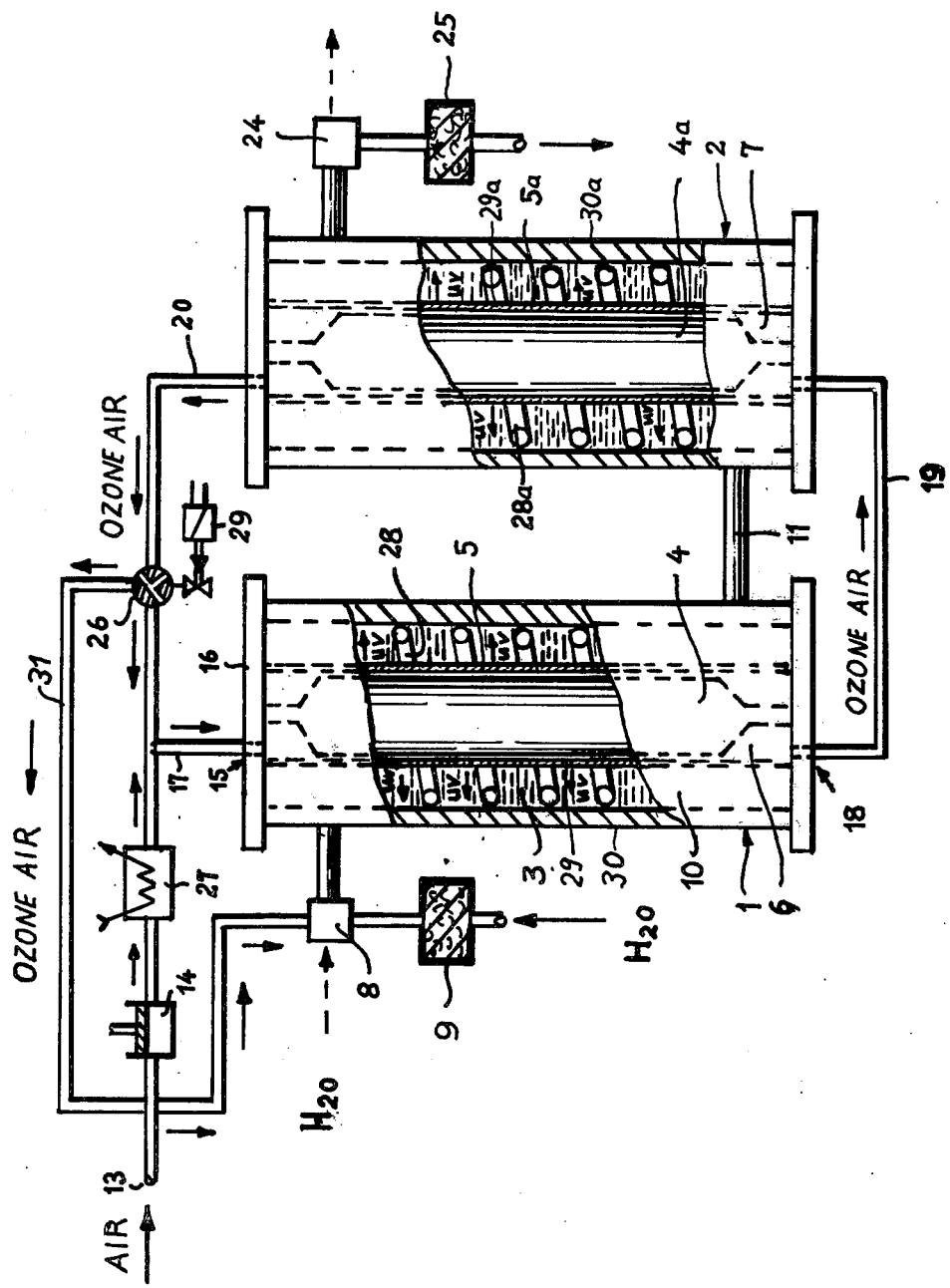

APPARATUS FOR STERILIZING FLUIDS WITH UV RADIATION AND OZONE

BACKGROUND OF THE INVENTION

This invention relates to an apparatus and a process for sterilizing fluids.

It has been proposed to provide an apparatus with a radiation chamber in which the disinfecting properties of both ultraviolet radiation and ozone are combined in order to sterilize fluids. The radiation chamber includes at least one source of ultraviolet radiation, and a housing having an outer casing spaced from a uv-permeable inner casing. The inner casing of the housing is spaced around the source in such a manner as to form an intermediary channel, and a fluid is conveyed through the space between the casings. The ultraviolet radiation forms ozone in the gas, and has a sterilizing effect in the fluid. The ozonized gas and the fluid emerging from the radiation chamber are then combined to a separate collector vessel.

The proposal mixes ozonized gas and fluid away from the radiation chamber. Because ozone is highly unstable and since the reaction which forms ozone as a product is reversible, this prior-art proposal fails to utilize the full ozonization capacity of the gas.

SUMMARY OF THE INVENTION

It is an object of the present invention to provide an extremely economical sterilizing unit by, on one hand, reducing the expense of the previously-described apparatus and, on the other hand, intensifying the sterilizing effect.

It is another object of the present invention to provide an apparatus in which the collector for the ozonized gas and fluid can be eliminated.

It is still another object of the present invention to provide an apparatus in which ozone and fluid are mixed within a radiation chamber so that ozone production continues as the ozone disinfects.

In accordance with the inventive concept, ozonized gas emerging from the channels of the radiation chamber is fed back into the radiation chamber by adding the gas to the fluid streaming through the space between the outer and inner casing. Consequently, a collector for the ozonized gas and the irradiated fluid is no longer required. In accordance with the invention, the sterilized fluid is withdrawn by way of a tap provided at the outlet of radiation chamber. After adding it to the fluid, the ozonized gas is subjected to renewed ultraviolet radiation. As a result, the ozonization is intensified, and therefore the sterilizing effect is improved.

The inventive concept includes returning ozonized gas to a radiation chamber by adding the ozonized gas to fluid entering the space between the outer and inner casings of the radiation chamber. The use of a three-way valve in another embodiment of the invention permits a relatively broad range of variation in the sterilizing effect while also making possible a further development of the inventive concept. The operation of a three-way valve allows at least portions of the ozonized gas to also flow through the channel between the inner casing and the source of radiation. This three-way valve can be manually manipulated or automatically regulated, for example by negative feedback.

Generally, the gas which is ozonized is air.

It is particularly advantageous to provide the apparatus with at least two radiation chambers which are connected in series in accordance with the flow of the fluid. In this embodiment the recirculating conduit leads from the radiation chamber at the end of the series to the radiation chamber at the beginning of the series and through which the gas first flowed.

A still further embodiment of the invention provides at least one baffle plate in the space between the outer and inner casing for the purpose of intensifying the sterilizing effect and also increasing the dwell time of the fluid in the radiation chamber. The baffle plate is preferably in the form of a helix; the helical form has the effect of imparting a twisting movement to the fluid.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

The single FIGURE is a schematic illustration of a preferred embodiment of the invention.

DESCRIPTION OF A PREFERRED EMBODIMENT

The single FIGURE illustrates a preferred embodiment of the inventive apparatus for sterilizing of fluid. The apparatus includes two ultraviolet radiation chambers 1, 2 which are connected in series in accordance with the flow of the fluids which are to be irradiated. An interchangeable source of ultraviolet radiation 4, 4a is provided within each of the radiation chambers 1, 2. The source of ultraviolet radiation 4, 4a is preferably a low pressure mercury vapor lamp; these are known per se.

In radiation chamber 1, the source of radiation 4 is spaced from and surrounded by a cylindrical housing 5. The housing 5 includes an inner casing 29 permeable to ultraviolet radiation and bounding a channel 6 with the source of radiation 4, and an outer casing 30 surrounding the inner casing 29 and forming a treating space 3 therewith. The casings of the housing 5 are preferably made of pure quartz glass. The space between the source 4 and the inner casing 29 (e.g., the width of the channel 6) is chosen in accordance with the desired efficiency of the radiation and/or the required wavelengths of radiation bombardment.

The fluids which are to be sterilized are fed into the radiation chamber 1 by way of the supply station 8, and preferably through the intermediary of a filter 9. The filter 9 removes from the fluid those substances and/or particles which would interfere with the permeability of the fluid to radiation of the desired wave range. The fluid arrives for a time inside the space 3 between the outer 30 and inner casings 29 of the housing 5, and flows from top to bottom in the first radiation chamber 1. The fluid in the radiation chamber 1 is subjected to bactericidal ultraviolet radiation of wavelengths within the range of 2000 to 3000 Å, particularly radiation of the wavelength of 254 nanometers. Radiation within this range is capable of radiating across the channel 6, penetrating the inner casing 29 of the housing 5, and irradiating the fluid.

In accordance with the preferred embodiment, a second radiation chamber 2 may be connected to radiation chamber 1. Radiation chamber 2 includes a source of radiation 4a spaced from and surrounded by a housing 5a. The housing 5a includes an inner casing 29a permeable to ultraviolet radiation and bounding a channel 7 with the source of radiation 4a and an outer casing 30a surrounding the inner casing 29a and forming a treating space 3a therewith. The casings 29a, 30a are preferably made of pure quartz glass. The space between source 4a and inner casing 29a is chosen in accordance with the desired efficiency of radiation and/or the required wavelength of radiation bombardment.

The fluid 10 which is subjected to the sterilizing effect of ultraviolet radiation in the first radiation chamber 1 arrives in the treating space 3a of the second radiation chamber 2 by way of a conduit 11. This fluid is irradiated in the second radiation chamber 2 with ultraviolet radiation of wavelengths 2000-3000 Å, particularly 254 nanometers and leaves the chamber 2 by way of the tap 24. A filter 25 can be connected to this tap; the filter 25 could be, for example, an active carbon filter.

A gas in which ozone can be formed (for example, air or another gas containing molecular oxygen) is added to the first radiation chamber 1 by way of an intake or inlet 13. An air compressor 14 or the like is preferably provided to conduct the gas into the radiation chamber 1. In order to improve the ozonization effect, the gas is preferably cooled. For this purpose, a cooler in the form of a Peltier element 27 or the like can be connected to the air compressor 14. The gas arrives in the first channel 6 by way of a conduit 17 penetrating the chamber cover 16 at the point 17.

As it travels downwardly in the channel 6 towards the outlet 18 of radiation chamber 1, the gas is exposed to wavelengths of ultraviolet radiation within the range of about 1800 to 2000 Å, but particularly the wavelength of 185 nanometers. This radiation ozonizes the gas. The ozonized gas streams from the bottom of radiation chamber 1 into the bottom of radiation chamber 2 by way of conduit 19. In radiation chamber 2, the gas travels upwardly through channel 7, in which the gas is subjected again to irradiation by the wavelengths of ultraviolet radiation within the range of about 1800 to 2000 Å, particularly 185 nanometers. Finally, the gas is conducted into conduit 20. Conduit 20 is connected to conduit 31 which leads back to the supply station 8 for the fluid. In supply station 8, the ozonized gas passing through conduits 20 and 31 is mixed with the fluid which is to be irradiated. By this mixing and the subsequent irradiation of the ozonized gas and the fluid, the sterilizing effects of ozone and ultraviolet radiation are combined. Of course, the ozonized gas can be introduced into the fluid spaces of radiation chamber 1 at points other than supply station 8.

The ozonized gas present in the conduit 20 can be resupplied once or even repeatedly to the channels 6 and 7 and thereafter recirculated to conduit 20 and fed into the fluid by means of a three-way valve 26 installed in the conduit 20. The three-way valve 26 can be automatically regulated by means of a solenoid valve 27 or the like. It is also within the inventive concept to feed only a portion of the ozonized gas again into channels 6 and 7 and to introduce the other portion directly into the fluid.

Helixes 28, 28a or the like are arranged within the spaces 3, 3a between the outer 30, 30a and inner 29, 29a casings of each of the radiation chambers 1, 2. These helically-shaped baffle plates 28, 28a contribute to the production of a spinning motion in the fluid. This spin increases the dwell time of the fluid in the radiation chambers 1, 2 and correspondingly improves the sterilizing effect. Of course, in special cases, even more radiation chambers can be connected parallel to each other.

It will be understood that each of the elements described above, or two or more together, may also find a useful application in other types of constructions differing from the types described above.

While the invention has been illustrated and described as embodied in an apparatus for sterilizing fluids, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

I claim:

1. An apparatus for sterilizing fluids, comprising a radiation chamber which comprises in combination, a source of ultraviolet radiation; a housing including an inner casing permeable to ultraviolet radiation and surrounding said source and bounding with the same a channel, and an outer casing surrounding said inner casing and forming a treating space therewith; means for conducting a stream of gas containing molecular oxygen through said channel for exposure to said ultraviolet radiation to produce an ozone-enriched gas; means for conducting a fluid through said treating space so as to become sterilized by the ultraviolet radiation; means for introducing at least a portion of said ozone-enriched gas from said channel into said treating space to become united with said fluid, whereby said introduced portion of ozone-enriched gas is again exposed to ultraviolet radiation in order to produce an increased content of ozone in said ozone-enriched gas and an additional sterilizing effect in said fluid; means connected to said channel for recirculating at least a portion of said ozone-enriched gas into said channel; and valve means connected to both said introducing means and said recirculating means and to said channel, said valve means being operative for selectively conducting desired portions of said ozone-enriched gas from said channel to said introducing means and said recirculating means, respectively.

2. An apparatus as defined in claim 1, said valve means comprising a three-way valve.

3. An apparatus as defined in claim 1, wherein said fluid conducting means includes an inlet conduit which is open into said treating space, said introducing means including a further conduit which communicates with and is open into said inlet conduit of said fluid conducting means.

4. An apparatus as defined in claim 1; further comprising another substantially similar chamber; means connecting said channel to a corresponding channel within said other radiation chamber for conducting said ozone-enriched gas from said radiation chamber to said other radiation chamber; and means connected to said corresponding channel for returning said ozone-enriched gas back into said radiation chamber.

5. An apparatus as defined in claim 4, said returning means being connected to said introducing means.

6. An apparatus as defined in claim 1; further comprising an interrupted baffle within said treating space.

7. An apparatus as defined in claim 6, said baffle is a helix so as to impart a spin to said fluid.

8. An apparatus as defined in claim 1; further comprising a cooler connected to said conducting means for cooling said stream of gas prior to entry of said stream of gas into said channel.

9. An apparatus as defined in claim 8, said cooler comprising a Peltier element.

* * * * *